US010870937B2

(12) United States Patent
Fiebig et al.

(10) Patent No.: US 10,870,937 B2
(45) Date of Patent: Dec. 22, 2020

(54) MELT-BLOWN WEBS WITHOUT SHOTS AND WITH IMPROVED BARRIER PROPERTIES

(71) Applicant: Borealis AG, Vienna (AT)

(72) Inventors: Joachim Fiebig, St. Marien (AT); Henk Van Paridon, Averbode (BE); Jingbo Wang, Linz (AT); Markus Gahleitner, Neuhofen/Krems (AT); Wilhelmus Henricus Adolf Sars, Tilburg (NL); Antti Tynys, Linz (AT)

(73) Assignee: BOREALIS AG, Vienna (AT)

(*) Notice: Subject to any disclaimer, the term of this patent is extended or adjusted under 35 U.S.C. 154(b) by 0 days.

(21) Appl. No.: 16/451,936

(22) Filed: Jun. 25, 2019

(65) Prior Publication Data

US 2019/0323155 A1    Oct. 24, 2019

Related U.S. Application Data

(62) Division of application No. 15/533,593, filed as application No. PCT/EP2015/079540 on Dec. 14, 2015, now abandoned.

(30) Foreign Application Priority Data

Dec. 15, 2014  (EP) .................... 14197889

(51) Int. Cl.
| | | |
|---|---|---|
| *D04H 1/56* | (2006.01) | |
| *C08K 5/3435* | (2006.01) | |
| *D04H 1/4291* | (2012.01) | |
| *D04H 1/544* | (2012.01) | |
| *C08K 5/103* | (2006.01) | |
| *C08F 8/50* | (2006.01) | |
| *D04H 3/16* | (2006.01) | |
| *D04H 3/007* | (2012.01) | |
| *D01F 1/10* | (2006.01) | |
| *D01F 6/06* | (2006.01) | |
| *A61B 46/00* | (2016.01) | |
| *A41D 13/12* | (2006.01) | |
| *A61F 13/51* | (2006.01) | |
| *C08K 5/098* | (2006.01) | |
| *C08F 4/654* | (2006.01) | |
| *C08F 4/651* | (2006.01) | |

(52) U.S. Cl.
CPC ............ *D04H 1/56* (2013.01); *A41D 13/1209* (2013.01); *A61B 46/40* (2016.02); *A61F 13/51* (2013.01); *C08F 8/50* (2013.01); *C08K 5/098* (2013.01); *C08K 5/103* (2013.01); *C08K 5/3435* (2013.01); *D01F 1/10* (2013.01); *D01F 6/06* (2013.01); *D04H 1/4291* (2013.01); *D04H 1/544* (2013.01); *D04H 3/007* (2013.01); *D04H 3/16* (2013.01); *C08F 4/651* (2013.01); *C08F 4/6546* (2013.01); *C08F 2810/10* (2013.01); *D10B 2321/022* (2013.01)

(58) Field of Classification Search
None
See application file for complete search history.

(56) References Cited

U.S. PATENT DOCUMENTS

| | | | |
|---|---|---|---|
| 5,723,217 | A | 3/1998 | Stahl et al. |
| 2004/0232578 | A1 | 11/2004 | Magni et al. |
| 2006/0128903 | A1 | 6/2006 | Roth et al. |
| 2013/0212993 | A1 | 8/2013 | Tynys et al. |
| 2013/0327006 | A1 | 12/2013 | Van Paridon et al. |

FOREIGN PATENT DOCUMENTS

| | | |
|---|---|---|
| EA | 201300546 | 11/2013 |
| EP | 0887379 | 12/1998 |
| EP | 1028984 | 7/2001 |
| EP | 2602367 | 6/2013 |
| EP | 2610271 | 7/2013 |
| EP | 2452960 | 11/2013 |
| EP | 2610270 | 10/2015 |
| EP | 2610272 | 5/2017 |
| KR | 1020130037713 | 4/2013 |
| WO | 9212182 | 7/1992 |
| WO | 9749737 | 12/1997 |
| WO | 9924478 | 5/1999 |
| WO | 9924479 | 5/1999 |
| WO | 0068315 | 11/2000 |
| WO | 0109113 | 11/2001 |
| WO | 2004000899 | 12/2003 |
| WO | 2004111095 | 12/2004 |
| WO | 2006027327 | 3/2006 |
| WO | 2007126994 | 11/2007 |
| WO | 2011092092 | 8/2011 |
| WO | 2012007430 | 1/2012 |
| WO | 2012064468 | 5/2012 |

OTHER PUBLICATIONS

Busico, et al., "Microstructure of polypropylene," Progress in Polymer Science, vol. 26, 2001, pp. 443-533, Elsevier.

(Continued)

*Primary Examiner* — Catherine S Branch
(74) *Attorney, Agent, or Firm* — Lowenstein Sandler LLP

(57) ABSTRACT

Melt-blown webs having no shots and improved barrier properties, whereby the melt-blown webs are made out of a so-called "controlled rheology" propylene (CR-PP), which was visbroken without any peroxide.

11 Claims, No Drawings

(56) References Cited

OTHER PUBLICATIONS

Busico, et al., "Alk-1-ene Polymerization in the Presence of a Monocyclopentadienyl Zirconium (iv) Acetamidinate Catalyst: Microstructural and Mechanistic Insights a," Macromolecular Rapid Commun., vol. 28, 2007, pp. 1128-1134, Wiley InterScience.

Busico, et al., "Full Assignment of the 13C NMR Spectra of Regioregular Polypropylenes: Methyl and Methylene Region," Macromolecules, vol. 30, 1997, pp. 6251-6263, American Chemical Society.

Gande, et al., "New Effects to Improve Function and Performance of Nonwoven Fabrics," Ciba Specialty Chemicals Inc., Fibertech 2005, Mar. 16, 2005.

Cheng, H.N., "C NMR Analysis of Ethylene-Propylene Rubbers," Macromolecules, vol. 17, 1984, pp. 1950-1955, American Chemical Society.

European Search Report for 14197889.0 dated May 6, 2015, 6 pgs.

Plastic Additives Handbook Zweifel (2001), 5th Edition; pp. 871-873 ; Coloration of Styrenic and Acrylic Polymers.

Lalevee, et al., "Thiyl Radical Generation in Thiol or Disulfide Containing Photosensitive Systesm," Macromolecular Journal, Macromolecular Chemistry and Physics, 2009, Wiley-VCH Verlag GmbH & Co. KgAa, Weinheim, wiley InterScience 210, pp. 311-319.

International Search Report and Written Opinion for PCT/EP2015/079540 dated Mar. 17, 2016, 15 pgs.

Office Action with translation for Taiwanese Application No. 104141888, 25 pages, date of search completion—Sep. 21, 2016.

Yan, et al., "Flexible Multifunction Instrument for Automated Nonwoven Web Structure Analysis", Textile Research Journal, The University of Tennessee, Textile Res. J. 69(11) pp. 795-804, Nov. 1999.

Resconi, et al., "Selectivity in Propene Polymerization with Metallocene Catalysts," Chem. Rev., vol. 100, 2000, pp. 1253-1345, American Chemical Society.

Wang, et al., "Structural Analysis of Ethylene/Propylene Copolymers Synthesized with a Constrained Geometry Catalyst," Macromolecules, vol. 33, 2000, pp. 1157-1162, American Chemical Society.

Zhou, et al., "A new decoupling method for accurate quantification of polyethylene copolymer composition and triad sequence distribution with 13C NMR," Journal of Magnetic Resonance, vol. 187, 2007, pp. 225-233, Elsevier.

Bresee et al., "Influence of Processing Conditions on Melt Blown Web Structure. Part III—Water Quench," INJ, pp. 27-35 (2005).

Office Action for U.S. Appl. No. 15/533,593, filed Mar. 1, 2019, 14 pages.

Korean Application No. 10-2017-7017241 Office Action dated May 8, 2018 with translation, 9 pages.

English Translation of Russian Office Action for Application No. 2017123946/04 dated Jul. 9, 2018, 6 pages.

MELT-BLOWN WEBS WITHOUT SHOTS AND WITH IMPROVED BARRIER PROPERTIES

The present invention is related to melt-blown webs having no shots and improved barrier properties. The melt-blown webs of the invention are made out of a so-called "controlled rheology" propylene (CR-PP), which was visbroken without the use of a peroxide.

BACKGROUND

A melt-blown web, being a non-woven structure consisting of melt-blown fibers, is typically made in a one-step process in which high-velocity air blows a molten thermoplastic resin from an extruder die tip onto a conveyor or take-up screen to form fine fibered self-bonding web.

The processing temperature is one factor in the final fabric properties. The "optimum" processing temperature is one at which ideal properties of the fabric are achieved such as low shot with good hand and high barrier properties, or good filtration properties.

Web quality is controlled by many factors such as the uniformity of the fiber distribution in the air stream and adjustment of other manufacturing variables such as processing temperature. Another factor controlling fabric quality is the properties of the polypropylene. Several defects can result from a poor selection of polymer physical properties such as roping, fly, and shot. Shots are pinpoint-sized polypropylene beads in the fabric that affect porosity, uniformity, and hand (texture) of the fabric, and are a principle cause of off-quality fabric.

The presence of shots decreases the hydrohead of the web, which is an indirect measure of the porosity and proportional to the liquid barrier of the fabric.

Melt-blown webs are widely used in hygiene and filtration industry, for which the key properties are the barrier properties, meaning hydrohead (water/liquid barrier) and filtration efficiency (with particles).

Although many types of polymers can be employed for melt-blown fibers and fabrics, polypropylene is one of the most commonly used polymers.

Polypropylenes are produced using heterogeneous Ziegler-Natta catalysts or metallocene catalysts. Generally, commercial PP resins have a broad Molecular Weight Distribution (MWD) as a result of the broad distribution of active sites on the catalyst. MWD is a difficult characteristic to control, especially when Ziegler-Natta catalysts are being used.

Because the MWD significantly determines the properties and the performance in processing, this characteristic must be controlled. Control of MWD of the PP in conventional reactors is difficult because it requires the addition of chain terminators and chain transfer agents. These operations decrease output of the reactor and are often uneconomical. Therefore, as an alternative, this control is accomplished via a post-reactor operation that is commonly known as degradation of polypropylene (PP).

The degradation of PP is a well-known procedure in polymer processing engineering and the plastics industry. Its importance is based on the fact that by thermally decomposing and, as a result, reducing the length of the carbon chain of the PP, one can obtain different products with controlled rheological properties. Because of that, these products are referred to as Controlled-Rheology Polypropylenes (CR-PP).

In general, it has been concluded that CR-PP resins have lower molecular weight, narrower MWD and reduced viscosity.

The process of degradation needs what is called a "radical initiator".

This is a chemical substance which—under particular circumstances—will promote the formation of free radicals inducing chain degradation. Especially for the PP resins, peroxides have dominated as free radical initiators; CR-PP resins have been produced industrially for years using reactive extrusion processes which employ peroxides as free radical initiators. But also the use of hydroxylamine esters as other source of free radicals is known since some years.

WO 97/49737 describes a process for reducing the molecular weight of polymers at temperatures above 280° C. using so-called NOR-HALS (HALS: Hindered Amino Light Stabilisers) compounds containing the group:

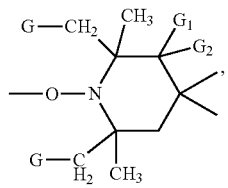

wherein G is hydrogen or methyl and G1 and G2 are each hydrogen, methyl or are together oxo. These known NOR-HALS compounds produce appreciable polymer degradation only at temperatures above 280° C.

WO 01/90113 discloses a process for reducing the molecular weight of polypropylene, propylene copolymers or polypropylene blends, wherein a hydroxylamine ester of the formula:

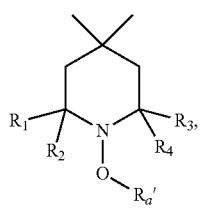

wherein among others Ra' is a monoacyl radical and R1-R4 are alkyl-substituents; is added to the polypropylene polymers to be degraded, and the mixture is heated to temperatures below 280° C.

According to WO 2007/126994 any hydroxylamine ester known in the art for reducing the molecular weight or visbreaking of polyolefin compounds, particularly propylene polymers, can be used. It is referred to WO 01/90113, where such suitable hydroxylamine esters are generally described. Furthermore it is stated that a preferable hydroxylamine ester is Irgatec® CR76, sold commercially by Ciba Speciality Chemicals Corporation (now by BASF). The degraded polypropylene is used for non-woven filter elements. WO 2007/126994 is silent about the problem of shot formation.

Furthermore EP 1 786 861 discloses the use of hydroxylamine esters as described in WO 01/90113, especially a hydroxylamine ester of formula

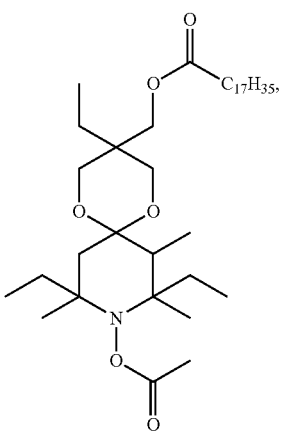

together with a sulphur compound, like Thio-Compound 1 ("Thio-1") of formula

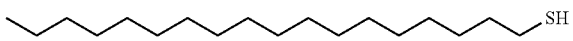 [SMILES: CCCCCCCCCCCCCCCCCCS]

for degrading polypropylene polymers at lower melt extrusion temperatures, like 250° C. EP 1 786 861 is completely silent about the use of such visbroken polymers for melt-blown webs and the problems of shot formation.

Normally for the manufacture of melt-blown fibers and webs polypropylene polymers are used which have been prepared by using Ziegler-Natta (ZN) catalysts; especially Ziegler-Natta (ZN) catalysts comprising a specific class of internal donors, namely phthalate compounds. However, some of these compounds are under suspicion of generating negative health and environmental effects and will probably be banned in the European Union in the future. Furthermore, there is an increasing demand on the market for "phthalate-free polypropylene" suitable for fiber applications in the hygiene/personal care market and in the filtration field.

On the other side, the performance of polypropylene non-woven webs based on melt-blown (MB) fibers or SMS fabrics (spunbonded/melt-blown/spunbonded) still needs to be improved.

For example, avoidance of shots and improved hydrohead (water barrier) of these systems are desired.

Thus, although melt-blown webs made out of called "controlled rheology" propylene (CR-PP), which was visbroken either by the use of peroxides or by the use of a hydroxylamine ester are known quite some years in the art, there is still a need for improvement of the web quality, by avoiding the presence of shots and improving the barrier properties.

SUMMARY OF THE PRESENT INVENTIONS

Thus, the present invention is in a first aspect directed to melt-blown webs comprising melt-blown fibers made of at least 80 wt % of a polypropylene composition comprising
  (A) a polypropylene polymer and
  (B) optionally a polymeric nucleating agent,
wherein the polypropylene composition has
  (i) a melt flow rate $MFR_2$ (230° C./2.16 kg) measured according to ISO 1133 of 20 to 5000 g/10 min or a molecular weight $M_w$ (measured with GPC) of below 180 000 g/mol, and
  (ii) a melting temperature Tm between ≥130° C. and ≤170° C. and
  (iii) a molecular weight distribution (MWD)>2 and
  (iv) wherein the polypropylene composition has been visbroken without the use of peroxide and
wherein the melt-blown web is free of shots and has a hydrohead (3rd drop, cm $H_2O$ resp. mbar), measured according to standard test WSP 80.6 (09), of a melt-blown web (produced with 270° C. melt temperature) having a weight per unit area of 9.5±1.0 g/m², of at least 80 mbar and of a melt-blown web (produced with 290° C. melt temperature) having a weight per unit area of 9.5±1.0 g/m², of at least 130 mbar.

According to a second aspect of the present invention, the polypropylene composition has been visbroken with a visbreaking ratio [final $MFR_2$ (230° C./2.16 kg)/initial $MFR_2$ (230° C./2.16 kg)] of 5 to 50, wherein "final $MFR_2$ (230° C./2.16 kg)" is the $MFR_2$ (230° C./2.16 kg) of the polypropylene composition after visbreaking and "initial $MFR_2$ (230° C./2.16 kg)" is the $MFR_2$ (230° C./2.16 kg) of the polypropylene composition before visbreaking.

According to a third aspect of the present invention the melt-blown web is characterized by the following ratios:
  (a) a molecular weight (Mw) ratio of Mw of the web to Mw of the polypropylene composition Mw(web)/Mw(PP) <1 and
  (b) a molecular weight distribution (MWD) ratio of MWD of the web to MWD of the polypropylene composition MWD(web)/MWD(PP)<1

According to a fourth aspect of the present invention the visbreaking was performed by using a hydroxylamine ester, a sulphur compound or by purely thermal degradation, preferably by using a hydroxylamine ester or a mercaptane compound and more preferably by using a hydroxyl amine ester.

In a further aspect of the present invention the polypropylene composition is free of phthalic compounds as well as their respective decomposition products.

In another aspect of the present invention, the polypropylene polymer has been polymerized in the presence of a) a Ziegler-Natta catalyst (ZN-C) comprising compounds (TC) of a transition metal of Group 4 to 6 of IUPAC, a Group 2 metal compound (MC) and an internal donor (ID), wherein said internal donor (ID) is preferably a non-phthalic compound, more preferably a non-phthalic acid ester; b) optionally a co-catalyst (Co), and c) optionally an external donor (ED). It is most preferred that a) the internal donor (ID) is selected from optionally substituted malonates, maleates, succinates, glutarates, cyclohexene-1,2-dicarboxylates, benzoates and derivatives and/or mixtures thereof, preferably the internal donor (ID) is a citraconate; b) the molar ratio of co-catalyst (Co) to external donor (ED) [Co/ED] is 5 to 45.

In yet another embodiment of the present invention, the polypropylene polymer is produced in at least one reactor (R1) or in a sequential polymerization process comprising at least two reactors (R1) and (R2), whereby in the first reactor (R1) a first polypropylene polymer fraction (PP1) is produced, which is subsequently transferred into the optional second reactor (R2), and wherein in the second reactor (R2) a second polypropylene polymer fraction (PP2) is produced in the presence of the first polypropylene polymer fraction (PP1).

The present invention is also directed to an article comprising the melt-blown web, wherein said article is selected from the group consisting of filtration media, diapers, sanitary napkins, panty liners, incontinence products for adults, protective clothing, breathing protection masks, surgical drapes, surgical gowns, und surgical wear in general.

The present invention is further directed to the use of a polypropylene composition as defined herein for improving the melt-blown web quality characterized by the absence of shots.

In the following the invention is described in more detail.

The polypropylene composition according to the present invention comprises as component (A) a propylene homopolymer and as optional component (B) a polymeric nucleating agent.

Component (A): Polypropylene Polymer

As component (A) a polypropylene polymer is used. Suitable polypropylene polymers are polypropylene homopolymers or random propylene copolymers, including terpolymers.

According to the present invention the expression "propylene homopolymer" relates to a polypropylene that consists substantially, i.e. of at least 99.0 wt %, more preferably of at least 99.5 wt %, still more preferably of at least 99.8 wt %, like of at least 99.9 wt %, of propylene units. In another embodiment only propylene units are detectable, i.e. only propylene has been polymerized.

The expression "random propylene copolymer" is preferably understood as a polypropylene comprising, preferably consisting of, units derivable from (a) propylene and (b) ethylene and/or $C_4$ to $C_{12}$ α-olefins.

Thus the propylene copolymer—or terpolymer according to this invention preferably comprises monomers copolymerizable with propylene, for example comonomers such as ethylene and/or $C_4$ to $C_{12}$ α-olefins, in particular ethylene and/or $C_4$ to $C_8$ α-olefins, e.g. 1-butene and/or 1-hexene. Preferably the propylene copolymer or terpolymer according to this invention comprises, especially consists of, monomers copolymerizable with propylene from the group consisting of ethylene, 1-butene and 1-hexene. More specifically the propylene copolymer or terpolymer of this invention comprises—apart from propylene—units derivable from ethylene and/or 1-butene. In a preferred embodiment the propylene copolymer according to this invention comprises units derivable from ethylene and propylene.

Additionally it is appreciated that the propylene copolymer or terpolymer preferably has a comonomer content is in the range of 1.0 to below 20.0 wt %, preferably in the range of 1.5 to below 10.0 wt %, more preferably in the range of 2.0 to below 9.5 wt %, still more preferably in the range of 2.5 to 9.0 wt %, yet more preferably in the range of 3.0 to 8.5 wt %.

One requirement of the polypropylene polymer (respectively composition) is a melt flow rate $MFR_2$ (230° C./2.16 kg) measured according to ISO 1133 in the range of 20 to 5000 g/10 min, preferably in the range of 30 to 3000 g/10 min, more preferably in the range of 150 to 2500 g/10 min, yet more preferably in the range of 400 and 2000 g/10 min.

Thus the polypropylene polymer (respectively composition) has a molecular weight $M_w$ (measured with GPC) after visbreaking of below 180 000 g/mol, preferably below 160 000 g/mol, more preferably below 150 000 g/mol and most preferably below 140 000 g/mol.

The polypropylene polymer (respectively the composition) suitable for the present invention is visbroken.

Thus the melt flow rate $MFR_2$ (230° C./2.16 kg) of the polypropylene polymer (respectively composition) before visbreaking is much lower, like from 2 to 500 g/10 min. For example, the melt flow rate $MFR_2$ (230° C./2.16 kg) of the polypropylene polymer (respectively composition) before visbreaking is from 3 to 450 g/10 min, like from 5 to 400 g/10 min.

Preferably the polypropylene polymer (respectively composition) has been visbroken with a visbreaking ratio [final $MFR_2$ (230° C./2.16 kg)/initial $MFR_2$ (230° C./2.16 kg)] of 5 to 50, wherein "final $MFR_2$ (230° C./2.16 kg)" is the $MFR_2$ (230° C./2.16 kg) of the polypropylene polymer (respectively composition) after visbreaking and "initial $MFR_2$ (230° C./2.16 kg)" is the $MFR_2$ (230° C./2.16 kg) of the polypropylene polymer (respectively composition) before visbreaking.

More preferably, the polypropylene polymer (respectively composition) has been visbroken with a visbreaking ratio [final $MFR_2$ (230° C./2.16 kg)/initial $MFR_2$ (230° C./2.16 kg)] of 5 to 25.

Even more preferably, the polypropylene polymer (respectively composition) has been visbroken with a visbreaking ratio [final $MFR_2$ (230° C./2.16 kg)/initial $MFR_2$ (230° C./2.16 kg)] of 5 to 15.

As mentioned above, it is an essential feature that the polypropylene polymer (respectively composition) has been visbroken.

Preferred mixing devices suited for visbreaking are known to an art skilled person and can be selected i.a. from discontinuous and continuous kneaders, twin screw extruders and single screw extruders with special mixing sections and co-kneaders and the like.

The visbreaking step according to the present invention is performed without any peroxide.

Preferably the visbreaking step is performed with a hydroxylamine ester or a mercaptane compound as source of free radicals (visbreaking agent) or by purely thermal degradation.

Preferably the visbreaking step is performed with a hydroxylamine ester or a sulphur compound as source of free radicals (visbreaking agent), more preferably the visbreaking step is performed with a hydroxylamine ester as source of free radicals (visbreaking agent).

By visbreaking the polypropylene polymer according to the present invention, the molar mass distribution (MWD) becomes narrower because the long molecular chains are more easily broken up or scissored and the molar mass M, will decrease, corresponding to an $MFR_2$ increase. The $MFR_2$ increases with increase in the amount of hydroxylamine ester or sulphur compound which is used.

Suitable visbreaking agent selected from the group of hydroxylamine esters are known in the state of the art, for example as described in WO 2007/126994, where it is stated that any hydroxylamine ester known in the art for reducing the molecular weight of or viscosity breaking, polyolefin compounds, particularly propylene polymers can be used. Such suitable hydroxylamine esters are generally described in WO 01/90113.

One preferred visbreaking agent selected from the group of hydroxylamine esters is Irgatec® CR76, sold commercially by Ciba Speciality Chemicals Corporation (now by BASF), which is also mentioned in WO 2007/126994.

Preferred hydroxylamine esters are compounds of the formula (I)

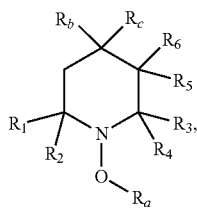

(I)

wherein $R_a$ represents acyl;

one of $R_b$ and $R_c$ represents hydrogen and the other one represents a substituent; or $R_b$ and $R_c$ both represent hydrogen or identical or different substituents; or $R_b$ and $R_c$ together represent oxygen;

$R_1$-$R_4$ each represent $C_1$-$C_6$alkyl; and $R_5$ and $R_6$ each represent independently of one another hydrogen, $C_1$-$C_6$alkyl or $C_6$-$C_{10}$aryl;

or $R_5$ and $R_6$ together represent oxygen.

In the hydroxylamine ester (I) the term acyl with regard to the definition of $R_a$ preferably represents an acyl radical selected from the group consisting of —C(=O)—H, —C(=O)—$C_1$-$C_{19}$alkyl, —C(=O)—$C_2$-$C_{19}$alkenyl, —C(=O)—$C_2$-$C_4$alkenyl-$C_4$-$C_{10}$aryl, —C(=O)—$C_6$-$C_{10}$aryl, —C(=O)—O—$C_1$-$C_6$alkyl, —C(=O)—O—$C_6$-$C_{10}$aryl, —C(=O)—NH—$C_1$-$C_6$alkyl, —C(=O)—NH$C_6$-$C_{10}$aryl and —C(=O)—N($C_1$-$C_6$alkyl)$_2$;

$C_1$-$C_{19}$alkyl in the acyl group $R_a$ is, for example, $C_1$-$C_6$alkyl, e.g. methyl, ethyl, n-propyl or isopropyl or n-, sec- or tert-butyl or straight-chain or branched pentyl or hexyl, or $C_7$-$C_{19}$alkyl, e.g. straight-chain or branched heptyl, octyl, isooctyl, nonyl, tert-nonyl, decyl or undecyl, or straight-chain $C_{11}$-$C_{19}$alkyl, which together with the —(C=O)— radical forms $C_{14}$-$C_{20}$alkanoyl having an even number of C-atoms, e.g. lauroyl ($C_{12}$), myristoyl ($C_{14}$), palmitoyl ($C_{16}$) or stearoyl ($C_{18}$).

$C_6$-$C_{10}$Aryl is, for example, carbocyclic monoaryl or diaryl, preferably monoaryl, e.g. phenyl, which may be monosubstituted or disubstituted by suitable substituents, e.g. $C_1$-$C_4$alkyl, e.g. methyl, ethyl or tert-butyl, $C_1$-$C_4$alkoxy, e.g. methoxy or ethoxy, or halogen, e.g. chlorine. In the case of disubstitution, the 2- and 6-positions are preferred.

The above-mentioned acyl radical Ra may be substituted on the free valences by suitable substituents, e.g. fluorine or chlorine, and is preferably formyl, acetyl, trifluoroacetyl, pivaloyl, acryloyl, methacryloyl, oleoyl, cinnamoyl, benzoyl, 2,6-xyloyl, tert-butoxycarbonyl, ethylcarbmoyl or phenylcarbamoyl.

$C_1$-$C_6$Alkyl as $R_1$-$R_4$ is preferably $C_1$-$C_4$alkyl, in particular $C_1$-$C_2$alkyl, e.g. methyl or ethyl.

In preferred embodiments, $R_1$-$R_4$ are methyl or ethyl. Alternatively, from one to three substituents $R_1$-$R_4$ are ethyl. The remaining substituents are then methyl.

$R_5$ and $R_6$ are preferably hydrogen. $C_1$-$C_6$Alkyl or $C_6$-$C_{10}$aryl as $R_5$ and $R_6$ are preferably methyl or phenyl.

The hydroxylamine esters (I) are known or can be prepared by known methods, e.g. by acylation of the corresponding >N—OH compound in a customary esterification reaction with an acid $R_a$—OH that introduces the group $R_a$ and corresponds to an acyl group selected, for example, from the group consisting of —C(=O)—H, —C(=O)—$C_1$-$C_{19}$alkyl, —C(=O)—$C_2$-$C_{19}$alkenyl, —C(=O)—$C_2$-$C_4$alkenyl-$C_6$-$C_{10}$aryl, —C(=O)—$C_6$-$C_{10}$aryl, —C(=O)—O—$C_1$-$C_6$alkyl, —C(=O)—O—$C_6$-$C_{10}$aryl, —C(=O)—NH—$C_1$-$C_6$alkyl, —C(=O)—NH—$C_6$-$C_{10}$aryl and —C(=O)—N($C_1$-$C_6$alkyl)$_2$, or a reactive functional derivative thereof, e.g. the acid halide Ra-X, e.g. the acid chloride, or anhydride, e.g. ($R_a$)$_2$O. The hydroxylamine esters (I) and methods for their preparation are described in WO 01/90113.

A preferred hydroxylamine ester (I) is selected from the group consisting of sterically hindered amine derivatives of the formula:

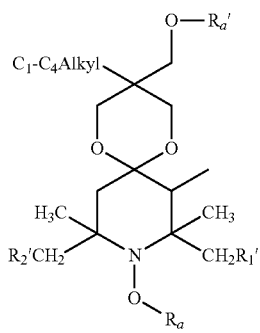

Wherein $R_1'$ and $R_2'$ independently of one another represent hydrogen or methyl;

$R_a$ represents $C_1$-$C_6$ alkanoyl; and $R_a'$ represents $C_8$-$C_{22}$alkanoyl.

According to a more preferred embodiment the hydroxylamine ester (I) is selected from the group consisting of sterically hindered amine derivatives of the formula:

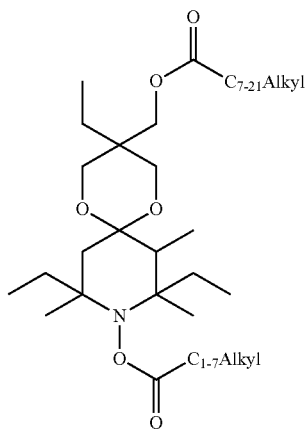

Most preferred is a compound of the above formula, in which the Alkylgroup is a $C_{17}$-group. Such a compound is commercially available under the tradename Irgatec® CR76.

Suitable amounts of hydroxylamine ester to be employed in accordance with the present invention are in principle known to the skilled person and can easily be calculated on the basis of the amount of polypropylene composition and/or propylene homopolymer to be subjected to visbreaking, the $MFR_2$ (230° C./2.16 kg) value of the polypropylene composition and/or the propylene homopolymer to be subjected to visbreaking and the desired target $MFR_2$ (230° C./2.16 kg) of the product to be obtained.

The hydroxylamine ester is preferably added in the form of a masterbatch containing these compounds in a polymer matrix in a concentration of, for example, from about 0.01 to 15% by weight, preferably from 0.05 to 8.0% by weight.

Suitable sulphur compounds are e.g. thiols of formula $R_1$—S—H and disulfides of formula $R_1$—S—S—$R_1$, known for example from EP 1 786 861 (thiols) or from Lalevée at al., Macromol. Chem. Phys. 2009, 210, 311-319 (thiols and disulfides).

The sulphur compounds are known or can be obtained by known methods.

An organic substituent $R_1$, which is attached to the sulphur atom(s) with a carbon atom, is, for example, $C_8$-$C_{22}$ alkyl, hydroxy-$C_2$-$C_8$ alkyl, mercapto-$C_2$-$C_8$ alkyl, mercapto-$C_8$-$C_{20}$ alkyl interrupted by at least one —NH—, mercapto-$C_8$-$C_{18}$ alkyl substituted by at least one hydroxy, $C_6$-$C_{10}$ aryl, $C_6$-$C_{10}$ aryl substituted by at least one substituent selected from the group consisting of $C_1$-$C_4$alkyl, 4-thiophenyl and 3-methyl-4-thiophenyl, or $C_6$-$C_{10}$aryl-$C_1$-$C_4$alkyl.

$R_1$ defined as $C_8$-$C_{22}$alkyl is straight-chain or branched $C_8$-C18 alkyl e.g. n-octyl, isooctyl types, e.g. 3,4-, 3,5- or 4,5-dimethyl-1-hexyl or 3- or 5-methyl-1-heptyl, other branched octyl types, such as 1,1,3,3-tetramethylbutyl or 2-ethylhexyl, n-nonyl, 1,1,3-trimethylhexyl, n-decyl, n-undecyl, 1-methylundecyl, 2-n-butyl-n-octyl, isotridecyl, 2-n-hexyln-decyl, 2-n-octyl-n-dodecyl or straight-chain $C_{12}$-$C_{19}$ alkyl, e.g. lauryl (C12), myristyl (C14), cetyl (C16) or n-octadecyl (C18).

$R_1$ defined as hydroxy-$C_2$-$C_8$ alkyl is, for example, 2-hydroxyethyl, 2- or 3-hydroxypropyl, 4-hydroxy-2-hexyl or 4-hydroxy-3-hexyl.

$R_1$ defined as mercapto-$C_2$-$C_8$ alkyl is, for example, $C_2$-$C_8$ alkyl substituted at the terminal carbon atom by a thiol (mercapto) group, e.g. 6-mercapto-n-hexyl or 5-mercapto-n-pentyl.

$R_1$ defined as $C_6$-$C_{10}$ aryl is preferably phenyl.

$R_1$ defined as $C_6$-$C_{10}$ aryl-$C_1$-$C_4$alkyl is, for example, benzyl, phen-1-ethyl or phenyl-2-ethyl.

Or $R_1$ which is attached to the sulphur atom(s) with a carbon atom can have the following structures

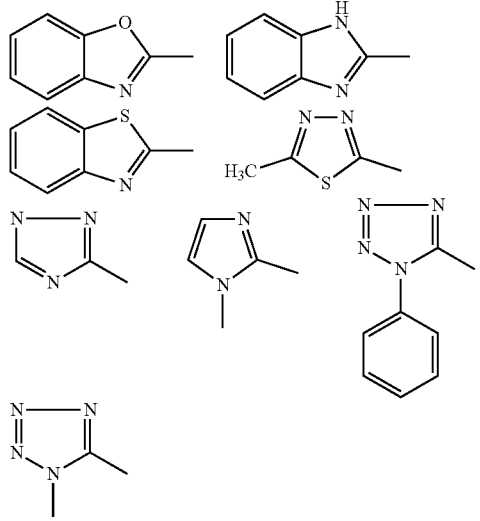

Preferred sulphur compounds are thiols, wherein $R_1$ is a straight-chain or branched $C_8$-$C_{18}$ alkyl.

Most preferred sulphur compound is 1-octadecan thiol.

The third variant for visbreaking is the purely thermal degradation. Conditions which are conducive to a degradation are: high temperature and/or the presence of oxygen.

Where the process is carried out in the absence of oxygen, the thermal degradation is preferably effected by heating the polymer at a temperature of from 250° C. to 350° C., preferably of from 270° C. to 310° C.

In the presence of oxygen it is preferably effected by heating the polymer at a temperature of from 150° C. to 180° C.

It is within the skill of an art skilled person to choose the right parameters for the purely thermal degradation to achieve the desired molecular weight distribution, respectively MFR$_2$ of the visbroken polypropylene polymer.

Preferably the visbreaking is done with the use of a hydroxylamine ester, as described above, or with the use of a sulphur compound, as described above.

More preferably the visbreaking is done with the use of a hydroxylamine ester.

Typically, visbreaking in accordance with the present invention is carried out in an extruder, so that under the suitable conditions, an increase of melt flow rate is obtained. During visbreaking, higher molar mass chains of the starting product are broken statistically more frequently than lower molar mass molecules, resulting as indicated above in an overall decrease of the average molecular weight and an increase in melt flow rate.

After visbreaking the polypropylene polymer (respectively composition) according to this invention is preferably in the form of pellets or granules.

The propylene homopolymer and the propylene copolymers are further defined by their microstructure.

Unless otherwise indicated, throughout the instant invention, the melting/crystallization behaviour, xylene cold soluble content (XCS), isotacticity and the amount of <2,1> regiodefects as defined below for the polypropylene composition and the propylene homopolymer or propylene copolymer, respectively, is preferably the melting/crystallization behaviour, xylene cold soluble content (XCS), isotacticity and the amount of <2,1> regiodefects of the polypropylene composition and the propylene homopolymer or propylene copolymer, respectively, after visbreaking.

Ad Propylene Homopolymer:

Preferably the propylene homopolymer is isotactic. Accordingly, it is preferred that the polypropylene homopolymer has a rather high pentad concentration (mmmm %) i.e. more than 90.0%, more preferably more than 93.0%, like more than 93.0 to 98.5%, still more preferably at least 93.5%, like in the range of 93.5 to 98.0%.

A further characteristic of the propylene homopolymer is the low amount of mis-insertions of propylene within the polymer chain, which indicates that the propylene homopolymer is produced in the presence of a Ziegler-Natta catalyst, preferably in the presence of a Ziegler-Natta catalyst (ZN-C) as defined in more detail below. Accordingly, the propylene homopolymer is preferably featured by low amount of 2,1 erythro regio-defects, i.e. of equal or below 0.4 mol %, more preferably of equal or below than 0.2 mol %, like of not more than 0.1 mol %, determined by 13C-NMR spectroscopy. In an especially preferred embodiment no 2,1 erythro regio-defects are detectable.

It is preferred that the propylene homopolymer is featured by rather high cold xylene soluble (XCS) content, i.e. by a xylene cold soluble (XCS) of at least 1.8 wt %, like at least 2.0 wt %.

Accordingly, the propylene homopolymer has preferably a xylene cold soluble content (XCS) in the range of 1.8 to 5.5 wt %, more preferably in the range of 2.0 to 5.0 wt %.

The amount of xylene cold solubles (XCS) additionally indicates that the propylene homopolymer is preferably free of any elastomeric polymer component, like an ethylene propylene rubber. In other words, the propylene homopolymer shall be not a heterophasic polypropylene, i.e. a system consisting of a polypropylene matrix in which an elastomeric phase is dispersed. Such systems are featured by a rather high xylene cold soluble content.

The propylene homopolymer suitable for the composition of this invention has no glass transition temperature below −30° C., preferably below −25° C., more preferably below −20° C.

In one preferred embodiment the propylene homopolymer suitable for the composition of this invention has a glass transition temperature in the range of −12° C. to 5° C., more preferably in the range of −10° C. to 4° C.

Further, the propylene homopolymer is preferably a crystalline propylene homopolymer. The term "crystalline" indicates that the propylene homopolymer has a rather high melting temperature. Accordingly throughout the invention the propylene homopolymer is regarded as crystalline unless otherwise indicated. Therefore, the propylene homopolymer has a melting temperature Tm measured by differential scanning calorimetry (DSC) in the range of ≥150° C. and ≤170° C., ppreferably in the range of 155° C. to 166° C.

Further it is preferred that the propylene homopolymer has a crystallization temperature Tc measured by differential scanning calorimetry (DSC) of equal or more than 110° C., more preferably in the range of 110° C. to 135° C., more preferably in the range of 114° C. to 130° C.

Preferably, the propylene homopolymer is obtained by polymerizing propylene in the presence of a Ziegler-Natta catalyst as defined below. More preferably, the propylene homopolymer according to this invention is obtained by a process as defined in detail below by using the Ziegler-Natta catalyst.

Additionally the propylene homopolymer has a molecular weight distribution (MWD) >2, like in the range from 2.1 to 10, preferably from 2.5 to 9.

The propylene homopolymer can comprise at least one propylene homopolymer fraction or two propylene homopolymer fractions, namely a first propylene homopolymer fraction (HPP1) and a second propylene homopolymer fraction (H-PP2). Preferably the weight ratio between the first propylene homopolymer fraction (H-PP1) and the second propylene homopolymer fraction (H-PP2) [(H-PP1):(H-PP2)] is 70:30 to 40:60, more preferably 65:35 to 45:55.

The first propylene homopolymer fraction (H-PP1) and the second propylene homopolymer fraction (H-PP2) may differ in the melt flow rate. However, it is preferred that the melt flow rate MFR2 (230° C.) of the first propylene homopolymer fraction (H-PP1) and of the second propylene homopolymer fraction (H-PP2) are nearly identical, i.e. differ not more than 15% as calculated from the lower of the two values, preferably differ not more than 10%, like differ not more than 7%.

Ad Propylene Copolymer

The propylene copolymer suitable according to this invention is preferably monophasic. Accordingly it is preferred that the propylene copolymer does not contain elastomeric (co)polymers forming inclusions as a second phase for improving mechanical properties. A polymer containing elastomeric (co)polymers as insertions of a second phase would by contrast be called heterophasic and is not part of the present invention. The presence of second phases or the so called inclusions are for instance visible by high resolution microscopy, like electron microscopy or atomic force microscopy, or by dynamic mechanical thermal analysis (DMTA). Specifically in DMTA the presence of a multiphase structure can be identified by the presence of at least two distinct glass transition temperatures.

Accordingly it is preferred that the propylene copolymer according to this invention has no glass transition temperature below −30, preferably below −25° C., more preferably below −20° C.

On the other hand, in one preferred embodiment the propylene copolymer according to this invention has a glass transition temperature in the range of −12 to +2° C., more preferably in the range of −10 to +2° C.

Further the propylene copolymer has a main melting temperature, i.e. a melting temperature representing more than 50% of the melting enthalpy, of at least 130° C., more preferably in the range of 133 to 155° C. still more preferably in the range of 134 to 152° C.

Further it is preferred that the propylene copolymer has a crystallization temperature of at least 110° C., more preferably in the range of 110 to 128° C., still more preferably in the range of 112 to 126° C., like in the range of 114 to 124° C.

Preferably, the propylene copolymer has a xylene cold soluble fraction (XCS) in the range of 3.0 to 25.0 wt %, preferably in the range of 4.5 to 20.0 wt %, more preferably in the range of 5.0 to 15.0 w %.

Preferably the propylene copolymer has a molecular weight distribution (Mw/Mn) of higher than 2.0, more preferably in the range of 2.1 to 6.0, still more preferably in the range of 2.5 to 5.5, like in the range of 3.1 to 5.3.

Summing up suitable polypropylene polymers have a melting temperature of ≥130° C. to ≤170° C. and a molecular weight distribution (MWD)>2.0.

Preferably the polypropylene polymers according to the present invention are propylene homopolymers.

The polypropylene polymer according to this invention is preferably produced in the presence of (a) a Ziegler-Natta catalyst (ZN-C) comprising compounds (TC) of a transition metal of Group 4 to 6 of IUPAC, a Group 2 metal compound (MC) and an internal donor (ID), wherein said internal donor (ID) is preferably a non-phthalic compound, more preferably a non-phthalic acid ester and still more preferably is a diester of nonphthalic dicarboxylic acids;

(b) optionally a co-catalyst (Co), and (c) optionally an external donor (ED).

It is preferred that the internal donor (ID) is selected from optionally substituted malonates, maleates, succinates, glutarates, cyclohexene-1,2-dicarboxylates, benzoates and derivatives and/or mixtures thereof, preferably the internal donor (ID) is a citraconate. Additionally or alternatively, the molar-ratio of co-catalyst (Co) to external donor (ED) [Co/ED] is 5 to 45.

Preferably, the polypropylene polymer is prepared by a polymerization process as further described below comprising at least one reactor (R1) and optionally a second reactor (R2), wherein in the first reactor (R1) the first polypropylene polymer fraction (PP1) is produced which is optionally subsequently transferred into the optional second reactor (R2), whereby in the second reactor (R2) the optional second polypropylene polymer fraction (PP2) is produced in the presence of the first polypropylene polymer fraction (PP1).

The process for the preparation of the polypropylene polymer as well as the Ziegler-Natta catalyst (ZN-C) used in said process are further described in detail below.

In view of the above, it is appreciated that the polypropylene polymer is free of phthalic compounds as well as their respective decomposition products, i.e. phthalic acid esters, typically used as internal donor of Ziegler-Natta (ZN) catalysts. Preferably, the polypropylene polymer is free of phthalic compounds as well as their respective decomposition products, i.e. phthalic compounds typically used as internal donor of Ziegler-Natta (ZN) catalysts.

The term "free of" phthalic compounds in the meaning of the present invention refers to a polypropylene polymer in which no phthalic compounds as well as no respective decomposition products at all originating from the used catalyst, are detectable.

According to the present invention the term "phthalic compounds" refers to phthalic acid (CAS No. 88-99-3), its mono- and diesters with aliphatic, alicyclic and aromatic alcohols as well as phthalic anhydride.

As the polypropylene composition is dominated by the polypropylene polymer the polypropylene composition is preferably also free of phthalic compounds as well as their respective decomposition products, more preferably of phthalic acid esters as well as their respective decomposition products.

For the same reasons, the values concerning melt flow rate (MFR2), xylene cold soluble content (XCS), isotacticity and the amount of <2,1> regiodefects as defined above for the polypropylene polymer are equally applicable for the polypropylene composition.

As already indicated above, the polypropylene polymer is optionally produced in a sequential polymerization process.

The term "sequential polymerization system" indicates that the polypropylene polymer is produced in at least two reactors connected in series. Accordingly, the polymerization system for sequential polymerization comprises at least a first polymerization reactor (R1) and a second polymerization reactor (R2), and optionally a third polymerization reactor (R3). The term "polymerization reactor" shall indicate that the main polymerization takes place. Thus, in case the process consists of two polymerization reactors, this definition does not exclude the option that the overall system comprises for instance a pre-polymerization step in a pre-polymerization reactor. The term "consist of" is only a closing formulation in view of the main polymerization reactors.

Preferably the first polymerization reactor (R1) is, in any case, a slurry reactor (SR) and can be any continuous or simple stirred batch tank reactor or loop reactor operating in bulk or slurry. Bulk means a polymerization in a reaction medium that comprises of at least 60% (w/w) monomer. According to the present invention the slurry reactor (SR) is preferably a (bulk) loop reactor (LR).

The optional second polymerization reactor (R2) can be either a slurry reactor (SR), as defined above, preferably a loop reactor (LR) or a gas phase reactor (GPR). The optional third polymerization reactor (R3) is preferably a gas phase reactor (GPR)

Suitable sequential polymerization processes are known in the state of the art.

A preferred multistage process is a "loop-gas phase"-process, such as developed by Borealis (known as BORSTAR® technology) described e.g. in patent literature, such as in EP 0 887 379, WO 92/12182 WO 2004/000899, WO 2004/111095, WO 99/24478, WO 99/24479 or in WO 00/68315.

A further suitable slurry-gas phase process is the Spheripol® process of Basell.

It is within the skill of art skilled persons to choose the polymerization conditions in a way to yield the desired properties of the polypropylene polymer.

The Ziegler-Natta Catalyst (ZN-C), the External Donor (ED) and the Co-Catalyst (Co)

As pointed out above in the specific process for the preparation of the polypropylene polymer as defined above a Ziegler-Natta catalyst (ZN-C) must be used. Accordingly the Ziegler-Natta catalyst (ZN-C) will be now described in more detail.

The catalyst used in the present invention is a solid Ziegler-Natta catalyst (ZN-C), which comprises compounds (TC) of a transition metal of Group 4 to 6 of IUPAC, like titanium, a Group 2 metal compound (MC), like a magnesium, and an internal donor (ID) being preferably a non-phthalic compound, more preferably a non-phthalic acid ester, still more preferably being a diester of non-phthalic dicarboxylic acids as described in more detail below. Thus, the catalyst is preferably fully free of undesired phthalic compounds. Further, the solid catalyst is free of any external support material, like silica or $MgCl_2$, but the catalyst is self-supported.

The Ziegler-Natta catalyst (ZN-C) can be further defined by the way as obtained. Accordingly, the Ziegler-Natta catalyst (ZN-C) is preferably obtained by a process comprising the steps of a)

$a_1$) providing a solution of at least a Group 2 metal alkoxy compound (Ax) being the reaction product of a Group 2 metal compound (MC) and a monohydric alcohol (A) comprising in addition to the hydroxyl moiety at least one ether moiety optionally in an organic liquid reaction medium; or $a_2$) a solution of at least a Group 2 metal alkoxy compound (Ax') being the reaction product of a Group 2 metal compound (MC) and an alcohol mixture of the monohydric alcohol (A) and a monohydric alcohol (B) of Formula ROH, optionally in an organic liquid reaction medium; or $a_3$) providing a solution of a mixture of the Group 2 alkoxy compound (Ax) and a Group 2 metal alkoxy compound (Bx) being the reaction product of a Group 2 metal compound (MC) and the monohydric alcohol (B), optionally in an organic liquid reaction medium; or $a_4$) providing a solution of Group 2 alkoxide of formula $M(OR_1)_n(OR_2)_mX_{2-n-m}$ or mixture of Group 2 alkoxides $M(OR_1)_nX_{2-n'}$ and $M(OR_2)_mX_{2-m'}$, where M is Group 2 metal, X is halogen, $R_1$ and $R_2$ are different alkyl groups of $C_2$ to $C_{16}$ carbon atoms, and $0 \leq n < 2$, $0 \leq m < 2$ and $n+m+(2-n-m)=2$, provided that both n and $m \neq 0$, $0 < n' \leq 2$ and $0 < m' \leq 2$; and b) adding said solution from step a) to at least one compound (TC) of a transition metal of Group 4 to 6 and c) obtaining the solid catalyst component particles, and adding a internal electron donor (ID), preferably a non-phthalic internal donor (ID), at any step prior to step c).

The internal donor (ID) or precursor thereof is added preferably to the solution of step a).

According to the procedure above the Ziegler-Natta catalyst (ZN-C) can be obtained via precipitation method or via emulsion (liquid/liquid two-phase system)—solidification method depending on the physical conditions, especially temperature used in steps b) and c).

In both methods (precipitation or emulsion-solidification) the catalyst chemistry is the same.

In precipitation method combination of the solution of step a) with at least one transition metal compound (TC) in step b) is carried out and the whole reaction mixture is kept at least at 50° C., more preferably in the temperature range of 55° C. to 110° C., more preferably in the range of 70° C. to 100° C., to secure full precipitation of the catalyst component in form of a solid particles (step c).

In emulsion-solidification method in step b) the solution of step a) is typically added to the at least one transition metal compound (TC) at a lower temperature, such as from −10 to below 50° C., preferably from −5 to 30° C. During agitation of the emulsion the temperature is typically kept at −10 to below 40° C., preferably from −5 to 30° C. Droplets of the dispersed phase of the emulsion form the active catalyst composition. Solidification (step c) of the droplets is suitably carried out by heating the emulsion to a temperature of 70 to 150° C., preferably to 80 to 110° C.

The catalyst prepared by emulsion-solidification method is preferably used in the present invention.

In a preferred embodiment in step a) the solution of $a_2$) or $a_3$) are used, i.e. a solution of (Ax') or a solution of a mixture of (Ax) and (Bx).

Preferably the Group 2 metal (MC) is magnesium.

The magnesium alkoxy compounds (Ax), (Ax') and (Bx) can be prepared in situ in the first step of the catalyst preparation process, step a), by reacting the magnesium compound with the alcohol(s) as described above, or said magnesium alkoxy compounds can be separately prepared magnesium alkoxy compounds or they can be even commercially available as ready magnesium alkoxy compounds and used as such in the catalyst preparation process of the invention.

Illustrative examples of alcohols (A) are monoethers of dihydric alcohols (glycol monoethers). Preferred alcohols (A) are $C_2$ to $C_4$ glycol monoethers, wherein the ether moieties comprise from 2 to 18 carbon atoms, preferably from 4 to 12 carbon atoms. Preferred examples are 2-(2-ethylhexyloxy)ethanol, 2-butyloxy ethanol, 2-hexyloxy ethanol and 1,3-propylene-glycol-monobutyl ether, 3-butoxy-2-propanol, with 2-(2-ethylhexyloxy)ethanol and 1,3-propylene-glycol-monobutyl ether, 3-butoxy-2-propanol being particularly preferred.

Illustrative monohydric alcohols (B) are of formula ROH, with R being straight-chain or branched $C_6$-$C_{10}$ alkyl residue. The most preferred monohydric alcohol is 2-ethyl-1-hexanol or octanol.

Preferably a mixture of Mg alkoxy compounds (Ax) and (Bx) or mixture of alcohols (A) and (B), respectively, are used and employed in a mole ratio of Bx:Ax or B:A from 8:1 to 2:1, more preferably 5:1 to 3:1.

Magnesium alkoxy compound may be a reaction product of alcohol(s), as defined above, and a magnesium compound selected from dialkyl magnesiums, alkyl magnesium alkoxides, magnesium dialkoxides, alkoxy magnesium halides and alkyl magnesium halides. Alkyl groups can be a similar or different $C_1$-$C_{30}$ alkyl, preferably $C_2$-$C_{10}$ alkyl. Typical alkyl-alkoxy magnesium compounds, when used, are ethyl magnesium butoxide, butyl magnesium pentoxide, octyl magnesium butoxide and octyl magnesium octoxide. Preferably the dialkyl magnesiums are used. Most preferred dialkyl magnesiums are butyl octyl magnesium or butyl ethyl magnesium.

It is also possible that magnesium compound can react in addition to the alcohol (A) and alcohol (B) also with a polyhydric alcohol (C) of formula R" $(OH)_m$ to obtain said magnesium alkoxide compounds. Preferred polyhydric alcohols, if used, are alcohols, wherein R" is a straight-chain, cyclic or branched $C_2$ to $C_{10}$ hydrocarbon residue, and m is an integer of 2 to 6.

The magnesium alkoxy compounds of step a) are thus selected from the group consisting of magnesium dialkoxides, diaryloxy magnesiums, alkyloxy magnesium halides, aryloxy magnesium halides, alkyl magnesium alkoxides, aryl magnesium alkoxides and alkyl magnesium aryloxides. In addition a mixture of magnesium dihalide and a magnesium dialkoxide can be used.

The solvents to be employed for the preparation of the present catalyst may be selected among aromatic and aliphatic straight chain, branched and cyclic hydrocarbons with 5 to 20 carbon atoms, more preferably 5 to 12 carbon atoms, or mixtures thereof. Suitable solvents include benzene, toluene, cumene, xylol, pentane, hexane, heptane, octane and nonane. Hexanes and pentanes are particular preferred.

Mg compound is typically provided as a 10 to 50 wt % solution in a solvent as indicated above. Typical commercially available Mg compound, especially dialkyl magnesium solutions are 20-40 wt % solutions in toluene or heptanes.

The reaction for the preparation of the magnesium alkoxy compound may be carried out at a temperature of 40° to 70° C. Most suitable temperature is selected depending on the Mg compound and alcohol(s) used.

The transition metal compound of Group 4 to 6 is preferably a titanium compound, most preferably a titanium halide, like $TiCl_4$.

The non-phthalic internal donor (ID) used in the preparation of the catalyst used in the present invention is preferably selected from (di)esters of non-phthalic carboxylic (di)acids, 1,3-diethers, derivatives and mixtures thereof. Especially preferred donors are diesters of mono-unsaturated dicarboxylic acids, in particular esters belonging to a group comprising malonates, maleates, succinates, citraconates, glutamics, cyclohexene-1,2-dicarboxylates and benzoates, and any derivatives and/or mixtures thereof. Preferred examples are e.g. substituted maleates and citraconates, most preferably citraconates.

In emulsion method, the two phase liquid-liquid system may be formed by simple stirring and optionally adding (further) solvent(s) and additives, such as the turbulence minimizing agent (TMA) and/or the emulsifying agents and/or emulsion stabilizers, like surfactants, which are used in a manner known in the art for facilitating the formation of and/or stabilize the emulsion. Preferably, surfactants are acrylic or methacrylic polymers. Particular preferred are unbranched $C_{12}$ to $C_{20}$ (meth)acrylates such as poly(hexadecyl)-methacrylate and poly(octadecyl)-methacrylate and mixtures thereof. Turbulence minimizing agent (TMA), if used, is preferably selected from α-olefin polymers of α-olefin monomers with 6 to 20 carbon atoms, like polyoctene, polynonene, polydecene, polyundecene or polydodecene or mixtures thereof. Most preferable it is polydecene.

The solid particulate product obtained by precipitation or emulsion-solidification method may be washed at least once, preferably at least twice, most preferably at least three times with an aromatic and/or aliphatic hydrocarbons, preferably with toluene, heptane or pentane. The catalyst can further be dried, as by evaporation or flushing with nitrogen, or it can be slurried to an oily liquid without any drying step.

The finally obtained Ziegler-Natta catalyst is desirably in the form of particles having generally an average particle size range of 5 to 200 μm, preferably 10 to 100. Particles are compact with low porosity and have surface area below 20 g/m², more preferably below 10 g/m². Typically the amount of Ti is 1 to 6 wt %, Mg 10 to 20 wt % and donor 10 to 40 wt % of the catalyst composition.

Detailed description of preparation of catalysts is disclosed in WO 2012/007430, EP2610271, EP 261027 and EP2610272 which are incorporated here by reference.

The Ziegler-Natta catalyst (ZN-C) is preferably used in association with an alkyl aluminum cocatalyst and optionally external donors.

As further component in the instant polymerization process an external donor (ED) is preferably present. Suitable external donors (ED) include certain silanes, ethers, esters, amines, ketones, heterocyclic compounds and blends of these. It is especially preferred to use a silane. It is most preferred to use silanes of the general formula $$R^a_p R^b_q Si(OR^c)_{(4-p-q)}$$

wherein $R^a$, $R^b$ and $R^c$ denote a hydrocarbon radical, in particular an alkyl or cycloalkyl group, and wherein p and q are numbers ranging from 0 to 3 with their sum p+q being equal to or less than 3. $R^a$, $R^b$ and $R^c$ can be chosen independently from one another and can be the same or different. Specific examples of such silanes are (tert-butyl)$_2$Si(OCH$_3$)$_2$, (cyclohexyl)(methyl)Si(OCH$_3$)$^2$, (phenyl)$_2$Si(OCH$_3$)$_2$ and (cyclopentyl)$_2$Si(OCH$_3$)$_2$, or of general formula $$Si(OCH_2CH_3)_3(NR^3R^4)$$

wherein $R^3$ and $R^4$ can be the same or different a represent a hydrocarbon group having 1 to 12 carbon atoms.

$R^3$ and $R^4$ are independently selected from the group consisting of linear aliphatic hydrocarbon group having 1 to 12 carbon atoms, branched aliphatic hydrocarbon group having 1 to 12 carbon atoms and cyclic aliphatic hydrocarbon group having 1 to 12 carbon atoms. It is in particular preferred that $R^3$ and $R^4$ are independently selected from the group consisting of methyl, ethyl, n-propyl, n-butyl, octyl, decanyl, iso-propyl, iso-butyl, iso-pentyl, tert.-butyl, tert.-amyl, neopentyl, cyclopentyl, cyclohexyl, methylcyclopentyl and cycloheptyl.

More preferably both $R^1$ and $R^2$ are the same, yet more preferably both $R^3$ and $R^4$ are an ethyl group.

Especially preferred external donors (ED) are the dicyclopentyl dimethoxy silane donor (D-donor) or the cyclohexylmethyl dimethoxy silane donor (C-Donor).

In addition to the Ziegler-Natta catalyst (ZN-C) and the optional external donor (ED) a co-catalyst can be used. The co-catalyst is preferably a compound of group 13 of the periodic table (IUPAC), e.g. organo aluminum, such as an aluminum compound, like aluminum alkyl, aluminum halide or aluminum alkyl halide compound. Accordingly, in one specific embodiment the co-catalyst (Co) is a trialkylaluminium, like triethylaluminium (TEAL), dialkyl aluminium chloride or alkyl aluminium dichloride or mixtures thereof. In one specific embodiment the co-catalyst (Co) is triethylaluminium (TEAL).

Preferably the ratio between the co-catalyst (Co) and the external donor (ED) [Co/ED] and/or the ratio between the co-catalyst (Co) and the transition metal (TM) [Co/TM] should be carefully chosen.

Accordingly,
(a) the mol-ratio of co-catalyst (Co) to external donor (ED) [Co/ED] must be in the range of 5 to 45, preferably is in the range of 5 to 35, more preferably is in the range of 5 to 25; and optionally
(b) the mol-ratio of co-catalyst (Co) to titanium compound (TC) [Co/TC] must be in the range of above 80 to 500, preferably is in the range of 100 to 350, still more preferably is in the range of 120 to 300.

Component (B): Polymeric Nucleating Agent

As optional component (B) a polymeric nucleating agent, preferably a polymer of vinyl compound, more preferably a polymeric nucleating agent obtainable by polyerizing vinylcycloalkane monomers or vinylalkane monomers can be used.

The polymeric nucleating agent is more preferably a polymerized vinyl compound according to the following formula $$CH_2=CH-CHR^1R^2 \qquad (II)$$

wherein $R^1$ and $R^2$ together form a 5- or 6-membered saturated, unsaturated or aromatic ring, optionally containing substituents, or independently represent an alkyl group comprising 1 to 4 carbon atoms, whereby in case $R^1$ and $R^2$ form on aromatic ring, the hydrogen atom of the —CHR$^1$R$^3$ moiety is not present.

Even more preferably, the polymeric nucleating agent is selected from: vinyl cycloalkane polymer, preferably vinyl cyclohexane (VCH) polymer, vinyl cyclopentane polymer, 3-methyl-1-butene polymer and vinyl-2-methyl cyclohexane polymer. The most preferred nucleating agent is vinyl cyclohexane (VCH) polymer.

As mentioned above, in a preferred embodiment, nucleating agent is a polymeric nucleating agent, more preferably a polymer of vinyl compound according to formula (I) as defined above, even more preferably vinyl cyclohexane (VCH) polymer.

The amount of nucleating agent preferably is not more than 10000 ppm by weight (means parts per million based on the total weight of the polypropylene composition (100 wt %), also abbreviated herein shortly as ppm), more preferably not more than 6000 ppm, even more preferably not more than 5000 ppm, based on the total weight of the polypropylene composition (100 wt %).

The amount of the nucleating agent still more preferably is not more than 500 ppm, preferably is from 0.025 to 200 ppm, and more preferably is from 0.1 to 200 ppm, more preferably is from 0.3 to 200 ppm, most preferably is from 0.3 to 100 ppm, based on the total weight of the polypropylene composition (100 wt %).

In the preferred embodiment the nucleating agent is a polymeric nucleating agent, most preferably a polymer of vinyl compound according to formula (II) as defined above, even more preferably vinyl cyclohexane (VCH) polymer as defined above, and the amount of said nucleating agent (B) is not more than 200 ppm, more preferably is from 0.025 to 200 ppm, and more preferably is from 0.1 to 200 ppm, more preferably is from 0.3 to 200 ppm, most preferably is from 0.3 to 100 ppm, based on the total weight of the polypropylene composition (100 wt %).

The nucleating agent may be introduced to the polypropylene polymer (A) e.g. during the polymerization process of the polypropylene polymer (A) or may be incorporated to the polypropylene polymer (A) by mechanical blending with a nucleated polymer, containing the polymeric nucleating agent (so-called master batch technology) or by mechanical blending of the polypropylene polymer (A) with the nucleating agent as such.

Thus, the nucleating agent can be introduced to the polypropylene polymer (A) during the polymerization process of the polypropylene polymer (A). The nucleating agent is preferably introduced to the polypropylene polymer (A) by first polymerizing the above defined vinyl compound according to formula (II) as defined above, even preferably vinyl cyclohexane (VCH), in the presence of a catalyst system as described above, comprising a solid Ziegler Natta catalyst component, a cocatalyst and optional external donor, and the obtained reaction mixture of the polymer of the vinyl compound according to formula (II) as defined above, even more preferably vinyl cyclohexane (VCH) polymer, and the catalyst system is then used for producing the polypropylene polymer (A).

The polymerization of the vinyl compound, e. g. VCH, can be done in any inert fluid that docs not dissolve the polymer formed (e. g. polyVCH). It is important to make sure that the viscosity of the final catalyst/polymerized vinyl compound/inert fluid mixture is sufficiently high to prevent the catalyst particles from settling during storage and transport.

The adjustment of the viscosity of the mixture can be done either before or after the polymerization of the vinyl compound. It is, e. g., possible to carry out the polymerization in a low viscosity oil and after the polymerization of the vinyl compound the viscosity can be adjusted by addition of a highly viscous substance. Such highly viscous substance can be a "wax", such as an oil or a mixture of an oil with a solid or highly viscous substance (oil-grease). The viscosity of such a viscous substance is usually 1,000 to 15,000 cP at room temperature. The advantage of using wax is that the catalyst storing and feeding into the process is improved. Since no washing, drying, sieving and transferring are needed, the catalyst activity is maintained.

The weight ratio between the oil and the solid or highly viscous polymer is preferably less than 5:1.

In addition to viscous substances, liquid hydrocarbons, such us isobutane, propane, pentane and hexane, can also be used as a medium in the modification step.

The polypropylenes produced with a catalyst modified with polymerized vinyl compounds contain essentially no free (unreacted) vinyl compounds. This means that the vinyl compounds shall be completely reacted in the catalyst modification step.

Further, the reaction time of the catalyst modification by polymerization of a vinyl compound should be sufficient to allow for complete reaction of the vinyl monomer, i. e. the polymerization is continued until the amount of unreacted vinyl compounds in the reaction mixture (including the polymerization medium and the reactants) is less than 0.5 wt %, in particular less than 2000 ppm by weight (shown by analysis). Thus, when the pre-polymerized catalyst contains a maximum of about 0.1 wt % vinyl compound, the final vinyl compound content in the polypropylene will be below the limit of determination using the GC-MS method (<0.01 ppm by weight). Generally, when operating on an industrial scale, a polymerization time of at least 30 minutes is required, preferably the polymerization time is at least 1 hour and in particular at least 5 hours. Polymerization times even in the range of 6 to 50 hours can be used. The modification can be done at temperatures of 10 to 70° C., preferably 35 to 65° C.

This catalyst modification step is known as BNT-technology and is performed during the above described pre-polymerization step in order to introduce the polymeric nucleating agent.

General preparation of such modified catalyst system vinyl compound (II) is disclosed e.g. in EP 1 028 984 or WO 01/90113.

In another embodiment the polymeric nucleating agent is added with the so called masterbatch technology, where an already nucleated polymer, preferably a propylene homopolymer, containing the polymeric nucleating agent (masterbatch) is blended with the polypropylene polymer (A).

Such a masterbatch is preferably prepared by polymerizing propylene in a sequential polymerization process.

The term "sequential polymerization system" indicates that the propylene homopolymer is produced in at least two reactors connected in series. Accordingly, the present polymerization system comprises at least a first polymerization reactor (R1) and a second polymerization reactor (R2), and optionally a third polymerization reactor (R3). The term "polymerization reactor" shall indicate that the main polymerization takes place. Thus, in case the process consists of two polymerization reactors, this definition does not exclude the option that the overall system comprises for instance a pre-polymerization step in a pre-polymerization reactor. The term "consist of" is only a closing formulation in view of the main polymerization reactors.

The produced propylene homopolymer, containing the polymeric nucleating agent, is the so called carrier polymer.

If the nucleating agent is added in the form of a masterbatch together with a carrier polymer, the concentration of the nucleating agent in the masterbatch is at least 10 ppm, typically at least 15 ppm. Preferably this nucleating agent is present in the masterbatch in a range of from 10 to 2000 ppm, more preferably more than 15 to 1000 ppm, such as 20 to 500 ppm.

As described above, the carrier polymer is preferably a propylene homopolymer, produced with a catalyst system as described above for component (A) and having an $MFR_2$ (230° C., 2.16 kg) in the range of 1.0 to 800 g/10 min, preferably 1.5 to 500 g/10 min, more preferably 2.0 to 200 g/10 min and most preferably 2.5 to 150 g/10 min.

More preferably, the carrier polymer is an isotactic propylene homopolymer having a melting point very similar to the above defined propylene homopolymer as component (A). Therefore, the carrier polymer has a melting temperature Tm measured by differential scanning calorimetry (DSC) of equal or more than 150° C., i.e. of equal or more than 150 to 168° C. more preferably of at least 155° C., i.e. in the range of 155 to 166° C.

If the nucleating agent is added in the form of a masterbatch, the amount of masterbatch added is in the range of 1.0 to 10 wt %, preferably 1.5 to 8.5 wt % and more preferably 2.0 to 7.0 wt %, based on the total weight of the polypropylene composition.

Polypropylene Composition

The inventive polypropylene composition comprises the above defined polypropylene polymer as component (A) and optionally the above defined polymeric nucleating agent as component (B).

Preferably the inventive polypropylene composition comprises as polypropylene polymer (A) a propylene homopolymer, as described above.

As mentioned above, values concerning melt flow rate ($MFR_2$), xylene cold soluble content (XCS), isotacticity and the amount of <2,1> regiodefects as defined above for the polypropylene polymer are equally applicable for the polypropylene composition.

The same is true for the melting temperature of the polypropylene polymer which is also equally applicable for the polypropylene composition.

The crystallization temperature of the nucleated polypropylene composition is higher than the crystallization temperature of the polypropylene polymer used as component (A), if the polymeric nucleating agent is added to the polypropylene polymer in the form of a masterbatch after the polymerization process for producing the polypropylene polymer.

If the polymeric nucleating agent is introduced to the polypropylene polymer by the use of a catalyst system modified by the BNT-technology as described above, the crystallization temperature of the polypropylene polymer is also equally applicable for the polypropylene composition.

The polypropylene composition of the present invention may comprise further components. However, it is preferred that the inventive polypropylene composition comprises as polymer components only the polypropylene polymer as defined in the instant invention. Accordingly, the amount of polypropylene polymer may not result in 100.0 wt % based on the total polypropylene composition. Thus, the remaining part up to 100.0 wt % may be accomplished by further additives known in the art. However, this remaining part shall be not more than 5.0 wt %, like not more than 3.0 wt % within the total polypropylene composition; not including the amount of the optional masterbatch for introducing the polymeric nucleating agent. For instance, the inventive polypropylene composition may comprise additionally small amounts of additives selected from the group consisting of antioxidants, stabilizers, fillers, colorants, nucleating agents and antistatic agents. In general, they are incorporated during granulation of the pulverulent product obtained in the polymerization. Accordingly, the polypropylene polymer constitutes at least to 95.0 wt %, more preferably at least 97.0 wt % to the total polypropylene composition.

In case the polypropylene polymer comprises another α-nucleating agent than the polymeric nucleating agent as described above, it is preferred that it is free of β-nucleating agents. Such alternative α-nucleating agent is preferably selected from the group consisting of (i) salts of monocarboxylic acids and polycarboxylic acids, e.g. sodium benzoate or aluminum tert-butylbenzoate, and (ii) dibenzylidenesorbitol (e.g. 1,3:2,4 dibenzylidenesorbitol) and $C_1$-$C_8$-alkyl-substituted dibenzylidenesorbitol derivatives, such as methyldibenzylidenesorbitol, ethyldibenzylidenesorbitol or dimethyldibenzylidenesorbitol (e.g. 1,3:2,4 di(methylbenzylidene) sorbitol), or substituted nonitol-derivatives, such as 1,2,3,-trideoxy-4,6:5,7-bis-O-[(4-propylphenyl)methylene]-nonitol, and (iii) salts of diesters of phosphoric acid, e.g. sodium 2,2'-methylenebis (4,6,-di-tert-butylphenyl) phosphate or aluminium-hydroxy-bis[2,2'-methylene-bis(4,6-di-t-butylphenyl)phosphate], and (iv) mixtures thereof.

Such additives are generally commercially available and are described, for example, in "Plastic Additives Handbook", pages 871 to 873, 5th edition, 2001 of Hans Zweifel.

The instant polypropylene composition is preferably used in pellet or granule form for the preparation of the melt-blown fibers and subsequently to the melt-blown web or article according to the invention.

Thus, the above described polypropylene composition is used for preparing melt-blown fibers. Such melt-blown fibers have an average filament fineness of not more than 5 µm.

Furthermore, the melt-blown fibers comprise at least 80.0 wt %, preferably at least 85.0 wt %, more preferably at least 90.0 wt %, still more preferably at least 95.0 wt % based on the total weight of the melt-blown fibers, most preferably consist of, of the polypropylene composition as defined above.

Thus a further component may be present in the melt-blown fibers according to the invention. Such further component is a further polymer, which is preferably also a polypropylene based polymer.

It is within the skill of an art skilled person to choose a suitable additional polymer in a way that the desired properties of the melt-blown webs are not negatively effected.

The present invention is directed to melt-blown webs (MBW), made of these melt-blown fibers. Accordingly the present invention is also directed to a melt-blown web comprising the melt-blown fibers made of the polypropylene composition as defined above.

Further, the present invention is also directed to an article selected front the group consisting of filtration media (filter), diapers, sanitary napkins, panty liners, incontinence products for adults, protective clothing, surgical drapes, surgical gown, and surgical wear in general, comprising the melt-blown web (MBW) according to the present invention, preferably in an amount of at least 80.0 wt %, more preferably in an amount of at least 95.0 wt %, based on the total weight of the article. In one embodiment of the present invention, the article consists of the melt-blown web (MBW).

The weight per unit area of the melt-blown web depends very much on the end use, however it is preferred that the melt-blown web has a weight per unit area of at least 1 g/m², preferably in the range from 1 to 250 g/m².

In case the melt-blown web according to the instant invention is produced as a single layer web (e.g. for air filtration purposes) it has a weight per unit area of at least 1 g/m², more preferably of at least 4 g/m², yet more preferably in the range of 7 to 250 g/m², still more preferably in the range of 8 to 200 g/m².

In case the melt-blown web according to the instant invention is produced as one part of a multi-layer construction like an SMS-web comprising, preferably consisting of, a spunbonded web layer, a melt-blown web layer and another spunbonded web layer (e.g. for hygienic application), the melt-blown web has a weight per unit area of at least 0.8 g/m², more preferably of at least 1 g/m², yet more preferably in the range of 1 to 30 g/m², still more preferably in the range of 1.3 to 20 g/m². Alternatively, the multi-layer construction can also include a multiplicity of melt-blown web layers and spunbonded web layers, such as a SSMMS construction.

The melt-blown web according to the invention being as a single layer web or a multi-layer construction as described above containing the melt-blown web can be furthermore combined with other layers, i.e. polycarbonate layers or the like, depending on the desired end use of the produced article.

The melt-blown webs according to the present invention are free of shots.

According to the present invention, a shot in a melt-blown web is defined as a defect, deformation or hole in the web caused by an agglomeration of the fiber-forming polymer, said agglomeration having an equivalent diameter from 10 to 1000 times bigger than the average diameter of the fibers.

Furthermore the melt-blown webs according to the present invention have a hydrohead (3rd drop, cm $H_2O$ resp. mbar), measured according to standard test WSP 80.6 (09), of a melt-blown web (produced with 270° C. melt temperature) having a weight per unit area of 9.5±1.0 g/m2, of at least 80 mbar, preferably of at least 85 mbar, and of a melt-blown web (produced with 290° C. melt temperature) having a weight per unit area of 9.5±1.0 g/m2, of at least 130 mbar, preferably at least 135 mbar.

Additionally the melt-blown webs are characterized by the following ratios (a) a molecular weight (Mw) ratio of Mw of the web to Mw of the polypropylene composition Mw(web)/Mw(PP) <1, preferably ≤0.90, more preferably ≤0.85, still more preferably ≤0.80 and (b) a molecular weight distribution (MWD) ratio of MWD of the web to MWD of the polypropylene composition MWD(web)/MWD(PP)<1, preferably ≤0.95, more preferably ≤0.90, still more preferably ≤0.85, and most preferably ≤0.80

The present invention further directed to the use of a polypropylene composition as defined herein for improving the melt-blown web quality characterized by the absence of shots.

EXPERIMENTAL PART

A. Measuring Methods

The following definitions of terms and determination methods apply for the above general description of the invention including the claims as well as to the below examples unless otherwise defined.

Quantification of Microstructure by NMR Spectroscopy

Quantitative nuclear-magnetic resonance (NMR) spectroscopy was used to quantify the isotacticity and regio-regularity of the propylene homopolymers.

Quantitative $^{13}C\{^{1}H\}$ NMR spectra were recorded in the solution-state using a Bruker Advance III 400 NMR spectrometer operating at 400.15 and 100.62 MHz for $^{1}H$ and $^{13}C$ respectively. All spectra were recorded using a $^{13}C$ optimised 10 mm extended temperature probehead at 125° C. using nitrogen gas for all pneumatics.

For propylene homopolymers approximately 200 mg of material was dissolved in 1,2-tetrachloroethane-$d_2$ (TCE-$d_2$). To ensure a homogenous solution, after initial sample preparation in a heat block, the NMR tube was further heated in a rotatary oven for at least 1 hour. Upon insertion into the magnet the tube was spun at 10 Hz. This setup was chosen primarily for the high resolution needed for tacticity distribution quantification (Busico, V., Cipullo, R., Prog. Polym. Sci. 26 (2001) 443; Busico, V.; Cipullo, R., Monaco, G., Vacatello, M., Segre, A. L., Macromolecules 30 (1997) 6251). Standard single-pulse excitation was employed utilising the NOE and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico. G., Macromol. Rapid Commun. 2007, 28, 11289). A total of 8192 (8k) transients were acquired per spectra.

Quantitative $^{13}C\{^{1}H\}$ NMR spectra were processed, integrated and relevant quantitative properties determined from the integrals using proprietary computer programs.

For propylene homopolymers all chemical shifts are internally referenced to the methyl isotactic pentad (mmmm) at 21.85 ppm.

Characteristic signals corresponding to regio defects (Resconi, L., Cavallo, L., Fait, A., Piemontesi, F., Chem. Rev. 2000, 100, 1253;; Wang, W-J., Zhu, S., Macromolecules 33 (2000), 1157; Cheng, H. N., Macromolecules 17(1984), 1950) or comonomer were observed.

The tacticity distribution was quantified through integration of the methyl region between 23.6-19.7 ppm correcting for any sites not related to the stereo sequences of interest (Busico, V., Cipullo. R., Prog. Polym. Sci. 26 (2001) 443; Busico, V., Cipullo, R., Monaco, G., Vacatello, M., Segre, A. L., Macromolecules 30 (1997) 6251).

Specifically the influence of regio-defects and comonomer on the quantification of the tacticity distribution was corrected for by subtraction of representative regio-defect and comonomer integrals from the specific integral regions of the stereo sequences.

The isotacticity was determined at the pentad level and reported as the percentage of isotactic pentad (mmmm) sequences with respect to all pentad sequences:

[mmmm] %=100*(mmmm/sum of all pentads)

The presence of 2,1 erythro regio-defects was indicated by the presence of the two methyl sites at 17.7 and 17.2 ppm and confirmed by other characteristic sites. Characteristic signals corresponding to other types of regio-defects were not observed (Resconi, L., Cavallo, L., Fait, A., Piemontesi, F., Chem. Rev. 2000, 100, 1253).

The amount of 2,1 erythro regio-defects was quantified using the average integral of the two characteristic methyl sites at 17.7 and 17.2 ppm:

$P_{21e}=(I_{e6}+I_{e8})/2$

The amount of 1,2 primary inserted propene was quantified based on the methyl region with correction undertaken for sites included in this region not related to primary insertion and for primary insertion sites excluded from this region:

$P_{12}=I_{CH3}+P_{12e}$

The total amount of propene was quantified as the sum of primary inserted propene and all other present regio-defects:

$P_{total}=P_{12}+P_{21e}$

The mole percent of 2,1 erythro regio-defects was quantified with respect to all propene: [21e]mol.-%=100*($P_{21e}/P_{total}$)

$MFR_2$ (230° C.) is measured according to ISO 1133 (230° C., 2.16 kg load). The $MFR_2$ of the polypropylene composition is determined on the granules of the material, while the $MFR_2$ of the melt-blown web is determined on cut pieces of a compression-molded plaque prepared from the web in a heated press at a temperature of not more than 200° C., said pieces having a dimension which is comparable to the granule dimension.

The xylene soluble fraction at room temperature (xylene cold soluble XCS, wt %): The amount of the polymer soluble in xylene is determined at 25° C. according to ISO 16152; $5^{th}$ edition; 2005 Jul. 1.

DSC analysis, melting temperature ($T_m$), melting enthalpy ($H_m$), crystallization temperature ($T_g$) and crystallization enthalpy ($H_c$): measured with a TA Instrument Q200 differential scanning calorimetry (DSC) on 5 to 7 mg samples. DSC is run according to ISO 11357/part 3/method C2 in a heat/cool/heat cycle with a scan rate of 10° C./min in the temperature range of −30 to +225° C. Crystallization temperature ($T_c$) and crystallization enthalpy ($H_c$) are determined from the cooling step, while melting temperature ($T_m$) and melting enthalpy ($H_m$) are determined from the second heating step respectively from the first heating step in case of the webs.

Number Average Molecular Weight ($M_n$), Weight Average Molecular Weight ($M_w$), ($M_w/M_n$=MWD) of Propylene Homopolymer Molecular weight averages Mw, Mn and MWD were determined by Gel Permeation Chromatography (GPC) according to ISO 16014-4:2003 and ASTM D 6474-99. A PolymerChar GPC instrument, equipped with infrared (IR) detector was used with 3×Olexis and 1×Olexis Guard columns from Polymer Laboratories and 1,2,4-trichlorobenzene (TCB, stabilized with 250 mg/L 2,6-Di tert butyl 1-4-methyl-phenol) as solvent at 160° C. and at a constant flow rate of 1 mL/min. 200 µL of sample solution were injected per analysis. The column set was calibrated using universal calibration (according to ISO 16014-2:2003) with at least 15 narrow MWD polystyrene (PS) standards in the range of 0.5 kg/mol to 11 500 kg/mol. Mark Houwink constants for PS, PE and PP used are as described per ASTM D 6474-99. All samples were prepared by dissolving the polymer sample to achieve concentration of ~1 mg/ml (at 160° C.) in stabilized TCB (same as mobile phase) for 2.5 hours for PP at max. 160° C. under continuous gently shaking in the autosampler of the GPC instrument. The MWD of the polypropylene composition is determined on the granules of the material, while the MWD of the melt-blown web is determined on a fiber sample from the web, both being dissolved in an analogous way.

Grammage of the Web

The unit weight (grammage) of the webs in g/m$^2$ was determined in accordance with ISO 536:1995.

Hydrohead

The hydrohead or water resistance as determined by a hydrostatic pressure test is determined according to the WSP (worldwide strategic partners) standard test WSP 80.6 (09) as published in December 2009. This industry standard is in turn based on ISO 811:1981 and uses specimens of 100 cm$^2$ at 23° C. with purified water as test liquid and a rate of increase of the water pressure of 10 cm/min. An H$_2$O column height of X cm in this test corresponds to a pressure difference of X mbar.

Air Permeability

The air permeability was determined in accordance with DIN ISO 9237 at a pressure difference of 100 Pa. This air permeability is defined as the velocity of an air flow passing perpendicularly through the web specimen.

Filtration Efficiency

Air filtration efficiency was determined based on EN 1822-3 for flat sheet filter media, using a test filter area of 400 cm$^2$. The particle retention was tested with a usual aerosol of di-ethyl-hexyl-sebacate (DEHS), calculating efficiency for the fraction with 0.4 µm diameter from a class analysis with 0.1 µm scale. An airflow of 16 m$^3 \cdot$h$^{-1}$ was used, corresponding to an airspeed of 0.11 m·s$^{-1}$.

Pressure Drop

The pressure drop was measured according to DIN ISO 9237 at an air speed (permeability) of 500 mm/s.

Shots

"Shot is a measure of the number of deformations, defects or holes in the formed polymer fabric. A defect can be, for example, an agglomeration of polymer material from 10 to 1000 times greater in diameter than the diameter of the fibers. Qualitative test methods for determining "shot" can be found in U.S. Pat. No. 5,723,217. Fabrics samples are pulled off the MB fabric roll at random and a section several feet long encompassing the full width of the fabric is cut from the roll. The samples are held against a backlit glass plate and visually rated from "1" to "5" according to the level of shot (1=no shot; "5"=very high level of shot). A set of photographs of MB fabrics containing shot levels corresponding to each category from 1 to 5 serve as standards for rating the fabrics. A shot value is then determined by counting the number of defects or holes per unit area. This can be done by, for example, viewing the fabric in a microscope and manually counting the number of shot per unit area. Also, see Yan, Z. and Bresec, R R., Flexible Multifunctional Instrument for Automated Nonwoven Web Structure Analysis, 69 TEXTILE RES. J. 795-804 (1999)."

B. Examples

The catalyst used in the polymerization process for the propylene homopolymer of the inventive example (IE-1) and the Comparative Example (CE-1) was prepared as follows:

Used Chemicals:

20% solution in toluene of butyl ethyl magnesium (Mg(Bu)(Et), BEM), provided by Chemtura 2-ethylhexanol, provided by Amphochem 3-Butoxy-2-propanol-(DOWANOL™ PnB), provided by Dow bis(2-ethylhexyl)citraconate, provided by SynphaBase TiCl$_4$, provided by Millenium Chemicals Toluene, provided by Aspokem Viscoplex® 1-254, provided by Evonik Heptane, provided by Chevron Preparation of a Mg Alkoxy Compound Mg alkoxide solution was prepared by adding, with stirring (70 rpm), into 11 kg of a 20 wt-% solution in toluene of butyl ethyl magnesium (Mg(Bu)(Et)), a mixture of 4.7 kg of 2-ethylhexanol and 1.2 kg of butoxypropanol in a 20 l stainless steel reactor. During the addition the reactor contents were maintained below 45° C. After addition was completed, mixing (70 rpm) of the reaction mixture was continued at 60° C. for 30 minutes. After cooling to room temperature 2.3 kg g of the donor bis(2-ethylhexyl)citraconate was added to the Mg-alkoxide solution keeping temperature below 25° C. Mixing was continued for 15 minutes under stirring (70 ppm).

Preparation of Solid Catalyst Component 20.3 kg of TiCl$_4$ and 1.1 kg of toluene were added into a 20 l stainless steel reactor. Under 350 rpm mixing and keeping the temperature at 0° C., 14.5 kg of the Mg alkoxy compound prepared in example 1 was added during 1.5 hours. 1.7 l of Viscoplex® 1-254 and 7.5 kg of heptane were added and after 1 hour mixing at 0° C. the temperature of the formed emulsion was raised to 90° C. within 1 hour. After 30 minutes mixing was stopped catalyst droplets were solidified and the formed catalyst particles were allowed to settle. After settling (1 hour), the supernatant liquid was siphoned away. Then the catalyst particles were washed with 45 kg of toluene at 90° C. for 20 minutes followed by two heptane washes (30 kg, 15 min). During the first heptane wash the temperature was decreased to 50° C. and during the second wash to room temperature.

The thus obtained catalyst was used along with triethyl-aluminium (TEAL) as co-catalyst and cyclohexylmethyl dimethoxy silane (C-Donor) as external donor.

The aluminium to donor ratio, the aluminium to titanium ratio and the polymerization conditions are indicated in tables 1 and 2.

Polymerization was performed in a polypropylene (PP) pilot plant, comprising only a loop reactor.

TABLE 1

Preparation of the propylene homopolymer (Component (A)) for IE1

| | | Component (A) |
|---|---|---|
| TEAL/Ti | [mol/mol] | 65 |

TABLE 1-continued

Preparation of the propylene homopolymer
(Component (A)) for IE1

|  |  | Component (A) |
|---|---|---|
| TEAL/Donor | [mol/mol] | 18.8 |
| Catalyst feed | [g/h] | 1.6 |
| Loop (H-PP1) |  |  |
| Time | [h] | 0.47 |
| Temperature | [° C.] | 70 |
| Pressure | [kPa] | 35 |
| $MFR_2$ | [g/10 min] | 77 |
| XCS | [wt %] | 4.9 |
| $H_2/C3$ ratio | [mol/kmol] | 3.7 |
| amount | [wt.-%] | 100 |
| Final |  |  |
| $MFR_2$ | [g/10 min] | 77 |
| XCS | [wt %] | 3.4 |
| Tm | [° C.] | 162 |
| Tc | [° C.] | 114 |
| Mw | [g/mol] | 135000 |
| MWD | [—] | 6.5 |

TABLE 2

Preparation of the propylene homopolymer
(Component (A)) for IE2 and IE3

|  |  | Component (A) |
|---|---|---|
| TEAL/Ti | [mol/mol] | 65 |
| TEAL/Donor | [mol/mol] | 18.8 |
| Catalyst feed | [g/h] | 1.6 |
| Loop (H-PP1) |  |  |
| Time | [h] | 0.47 |
| Temperature | [° C.] | 70 |
| Pressure | [kPa] | 35 |
| $MFR_2$ | [g/10 min] | 3.5 |
| XCS | [wt %] | 3.5 |
| $H_2/C3$ ratio | [mol/kmol] | 0.7 |
| amount | [wt %] | 100 |
| Final |  |  |
| $MFR_2$ | [g/10 min] | 3.7 |
| XCS | [wt.-%] | 3.5 |
| Tm | [° C.] | 162 |
| Tc | [° C.] | 113 |
| Mw | [g/mol] | 320000 |
| MWD |  | 7.2 |

The propylene homopolymer has been mixed with 400 ppm calcium Stearate (CAS No. 1592-23-0) and 1,000 ppm Irganox 1010 supplied by BASF AG, Germany (Pentaerythrityl-tetrakis(3-(3',5'-di-tert.butyl-4-hydroxyphenyl)-propionate, CAS No. 6683-19-8).

In a second step the propylene homopolymer has been visbroken by using a co-rotating twin-screw extruder at 200-230° C. and using 1.1 wt % of Irgatec® CR76 (hydroxylamine ester in a polymer matrix; sold by BASF) (IE2) to achieve the target $MFR_2$ of 800 g/10 min.

For IE-2 0.075 wt % of 1-octadecanthiol and for IE-3 0.12 wt % of 2-octadecanthiol (supplied by Sigma Aldrich) were used.

TABLE 3

Properties of visbroken PP of IE2 and
IE3 (reference is without visbreaking)

| Example | unit | reference | IE2 | IE3 |
|---|---|---|---|---|
| 1-octadecanthiol | [wt %] | 0 | 0.075 | 0.12 |
| $MFR_2$ | [g/10 min] | 3.7 | 27.2 | 38.2 |
| Mw | [g/mol] | 320000 | 177500 | 156000 |
| MWD | [—] | 7.2 | 4.8 | 4.5 |

For Comparative Example CE1 the above produced propylene homopolymer including the additives as described above has been visbroken by using a co-rotating twinscrew extruder at 200-230° C. and using an appropriate amount (1750 ppm) of (tert.-butylperoxy)-2,5-dimethylhexane (Trigonox 101, distributed by Akzo Nobel, Netherlands) to achieve the target MFR2 of 800 g/10 min.

For Comparative Example CE2 polymerization was performed with catalyst Avant ZN L1, commercially available from Basell. The catalyst contains a phthalate based internal donor. The catalyst was used along with triethyl-aluminium (TEAL) as co-catalyst and cyclohexylmethyl dimethoxy silane (C-Donor) as external donor. Polymerization was performed in a PP pilot plant, comprising only a loop reactor.

TABLE 4

Preparation of the propylene homopolymer
(Component (A)) for CE2

|  |  | Component (A) |
|---|---|---|
| TEAL/Ti | [mol/mol] | 65 |
| TEAL/Donor | [mol/mol] | 18.8 |
| Catalyst feed | [g/h] | 1.3 |
| Loop (H-PP1) |  |  |
| Time | [h] | 0.5 |
| Temperature | [° C.] | 70 |
| Pressure | [kPa] | 35 |
| $MFR_2$ | [g/10 min] | 76 |
| XCS | [wt.-%] | 3.2 |
| $H_2/C3$ ratio | [mol/kmol] | 4.3 |
| amount | [wt.-%] | 100 |
| Final |  |  |
| Tm | [° C.] | 162 |
| Tc | [° C.] | 116 |
| Mw | [g/mol] | 133500 |
| MWD |  | 7.6 |

The propylene homopolymer for CE2 has been mixed with 400 ppm calcium Stearate (CAS No. 1592-23-0) and 1,000 ppm Irganox 1010 supplied by BASF AG, Germany (Pentaerythrityl-tetrakis(3-(3',5'-di-tert.butyl-4-hydroxyphenyl)-propionate, CAS No. 6683-19-8).

In a second step the propylene homopolymer has been visbroken by using a co-rotating twin-screw extruder at 200-230° C. and using 1.1 wt % of Irgatec® CR76 (hydroxylamine ester in a polymer matrix; sold by BASF) yielding Mw of 131000 and MWD 6.0.

The polypropylene compositions of IE1, CE1 and CE2 have been converted into melt-blown webs on a Reicofil MB250 line using a spinneret having 470 holes of 0.4 mm exit diameter and 35 holes per inch. Webs were produced at different melt temperatures, throughputs, DCD (die to collector distance) and air volumes.

The processing conditions for and properties of the melt-blown webs are indicated in tables 5 6, 7 and 8.

TABLE 5

Processing conditions for the production of the melt-blown webs

| Example | Melt Temperature °C. | DCD mm | Air volume m³/h | Throughput kg/h · m | Web weight g/m² |
|---|---|---|---|---|---|
| IE1-1 | 270 | 200 | 360 | 10 | 9.4 |
| IE1-2 | 290 | 200 | 210 | 10 | 9.4 |
| CE1-1 | 250 | 200 | 410 | 10 | 9.5 |
| CE1-2 | 270 | 200 | 300 | 10 | 9.3 |
| CE2-1 | 270 | 200 | 520 | 10 | 10.0 |
| CE2-2 | 290 | 200 | 310 | 10 | 10.0 |

TABLE 6

Properties of the melt-blown webs

| Example | Air permeability mm/s | Pressure drop Pa | Filtration Efficiency % | Quality factor 100/Pa | Hydrohead (3$^{rd}$ drop) cm H$_2$O* |
|---|---|---|---|---|---|
| IE1-1 | 823 | 57.4 | 25.08 | 0.504 | 88 |
| IE1-2 | 485 | 122.1 | 48.67 | 0.547 | 136.2 |
| CE1-1 | 952 | 44.3 | 25.47 | 0.664 | 74.7 |
| CE1-2 | 752 | 60.4 | 30.56 | 0.605 | 50.5 |
| CE2-1 | 1100 | 36.5 | 29.0 | 0.635 | 70.1 |
| CE2-2 | 1215 | 32 | 19.88 | 0.593 | 20.5 |

*also mbar

TABLE 7

MFR, Mw, MWD and shots for IE1 and CE1 on web

| | MFR (web) | Mw (web) | Mw (PP)* | Mw(web)/ Mw(PP) | MWD (web) | MWD (PP)** | MWD(web)/ MWD(PP) | Shots $^{a)}$ |
|---|---|---|---|---|---|---|---|---|
| IE1-1 | 860 | 62300 | 137000 | 0.45 | 3.9 | 6.0 | 0.65 | No (1) |
| IE2-1 | 1806 | 50400 | 137000 | 0.37 | 3.5 | 6.0 | 0.58 | No (1) |
| CE1-1 | 850 | 64000 | 67350 | 0.95 | 4.1 | 4.2 | 0.98 | yes (2) |
| CE1-2 | 1044 | 60000 | 67350 | 0.89 | 4 | 4.2 | 0.95 | Yes (4) |

*Mw measured on the visbroken PP granules
**MWD for the visbroken PP
$^{a)}$ rating 1 = no shots; rating 2 = low level of shots; rating 4 = high level of shots As can be seen from Table 3, 4 and 5 that at the same throughput, the polymer of the Inventive Example (visbroken with Irgatec®; IE1-1 and IE1-2) can go to higher melt temperature without producing shots in the web than the polymer of the Comparative Example (visbroken with peroxide; CE1-1 and CE1-2). (Polymers of IE1 and CE1 produced with the same catalyst, but different visbreaking agents used).

Furthermore it can be seen that the use of the polymer of the Inventive Example (visbroken with Irgatec®; IE1-1 and IE1-2) yields webs with improved water barrier properties, as can be seen in the higher hydrohead values compared to the comparative examples CE1 and CE2.

What is claimed is:

1. A method of preparing a melt-blown web which is free of shots, the method comprising blowing a molten polypropylene composition from an extruder die tip onto a conveyer or take-up screen, wherein the polypropylene composition comprises
    (A) a propylene polymer and
    (B) optionally a polymeric nucleating agent,
    wherein the polypropylene composition has
        (i) a melt flow rate MFR2 (230° C./2.16 kg) measured according to ISO 1133 of 20 to 5000 g/10min and
        (ii) a melting temperature Tm between ≥130° C. and ≤170° C. and
        (iii) a molecular weight distribution (MWD)>2
        (iv) wherein the propylene polymer has been polymerized in the presence of a) a Ziegler-Natta catalyst (ZN-C) comprising compounds (TC) of a transition metal of Group 4 to 6 of IUPAC, a Group 2 metal compound (MC) and an internal donor (ID), b) optionally a co-catalyst (Co), and c) optionally an external donor (ED), and
        (v) wherein the polypropylene composition has been visbroken without the use of peroxides.

2. The method of preparing a melt-blown web according to claim 1, wherein the propylene polymer is a propylene homopolymer.

3. The method of preparing a melt-blown web according to claim 1, wherein the polypropylene composition has been visbroken by using a hydroxylamine ester, a sulphur compound, or by purely thermal degradation.

4. The method of preparing a melt-blown web according to claim 3, wherein the polypropylene composition has been visbroken by using a hydroxylamine ester.

5. The method of preparing a melt-blown web according to claim 1, wherein the polypropylene composition is free of phthalic compounds as well as their respective decomposition products.

6. The method of preparing a melt-blown web according to claim 1, wherein the melt-blown web is characterized by the following ratios:
    (a) a molecular weight (Mw) ratio of Mw of the web to Mw of the polypropylene composition Mw(web)/Mw(PP)<1 and
    (b) a molecular weight distribution (MWD) ratio of MWD of the web to MWD of the polypropylene composition MWD(web)/MWD(PP)<1.

7. The method of preparing a melt-blown web according to claim 6, wherein the melt-blown web is characterized by the following ratios:
    (a) a molecular weight (Mw) ratio of Mw of the web to Mw of the polypropylene composition Mw(web)/Mw(PP) is ≤0.90, and
    (b) a molecular weight distribution (MWD) ratio of MWD of the web to MWD of the polypropylene composition MWD(web)/MWD(PP) is ≤0.95.

8. The method of preparing a melt-blown web according to claim 7, wherein the melt-blown web is characterized by the following ratios:
    (a) a molecular weight (Mw) ratio of Mw of the web to Mw of the polypropylene composition Mw(web)/Mw(PP) is ≤0.85, and
    (b) a molecular weight distribution (MWD) ratio of MWD of the web to MWD of the polypropylene composition MWD(web)/MWD(PP) is ≤0.90.

9. The method of preparing a melt-blown web according to claim 7, wherein the melt-blown web is characterized by the following ratios:
   (a) a molecular weight (Mw) ratio of Mw of the web to Mw of the polypropylene composition Mw(web)/Mw (PP) is ≤0.80, and
   (b) a molecular weight distribution (MWD) ratio of MWD of the web to MWD of the polypropylene composition MWD(web)/MWD(PP) is ≤0.85.

10. The method of preparing a melt-blown web according to claim 1, wherein the internal donor (ID) is selected from the group consisting of optionally substituted malonates, maleates, succinates, glutarates, cyclohexene-1,2-dicarboxylates, benzoates, derivatives thereof and mixtures thereof; and the molar ratio of co-catalyst (Co) to external donor (ED) [Co/ED] is 5 to 45.

11. The method of preparing a melt-blown web according to claim 1, wherein the Ziegler-Natta catalyst (ZN-C) is produced by a process comprising the steps of
   a)
      $a_1$) providing a solution of at least a Group 2 metal alkoxy compound (Ax) being the reaction product of a Group 2 metal compound (MC) and a monohydric alcohol (A) comprising in addition to the hydroxyl moiety at least one ether moiety optionally in an organic liquid reaction medium; or
      $a_2$) a solution of at least a Group 2 metal alkoxy compound (Ax') being the reaction product of a Group 2 metal compound (MC) and an alcohol mixture of the monohydric alcohol (A) and a monohydric alcohol (B) of formula ROH, optionally in an organic liquid reaction medium; or
      $a_3$) providing a solution of a mixture of the Group 2 alkoxy compound (Ax) and a Group 2 metal alkoxy compound (Bx) being the reaction product of a Group 2 metal compound (MC) and the monohydric alcohol (B), optionally in an organic liquid reaction medium; or
      $a_4$) providing a solution of Group 2 alkoxide of formula $M(OR_1)_m(OR_2)_m X_{2-n-m}$ or mixture of Group 2 alkoxides $M(OR_1)_n X_{2-n}$ and $M(OR_2)_m X_{2-m'}$, where M is Group 2 metal, X is halogen, $R_1$ and $R_2$ are different alkyl groups of $C_2$ to $C_{16}$ carbon atoms, and $0 \leq n < 2$, $0 \leq m < 2$ and $n+m+(2-n-m)=2$, provided that both n and m≠0, $0 < n' \leq 2$ and $0 < m' \leq 2$; and
   b) adding said solution from step a) to at least one compound (TC) of a transition metal of Group 4 to 6 and
   c) obtaining the solid catalyst component particles, and adding an internal electron donor (ID), at any step prior to step c).

* * * * *

UNITED STATES PATENT AND TRADEMARK OFFICE
CERTIFICATE OF CORRECTION

PATENT NO. : 10,870,937 B2
APPLICATION NO. : 16/451936
DATED : December 22, 2020
INVENTOR(S) : Fiebig et al.

Page 1 of 1

It is certified that error appears in the above-identified patent and that said Letters Patent is hereby corrected as shown below:

In the Claims

In Claim 11, Column 32, Line 14, delete "$M(OR_1)_m(OR_2)_mX_{2-n-m}$" and insert --$M(OR_1)_n(OR_2)_mX_{2-n-m}$--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*